United States Patent
Pickett (10) Patent No.: US 10,772,567 B2
(45) Date of Patent: Sep. 15, 2020

(54) FREQUENCY DOMAIN ADAPTIVE MOTION CANCELLATION FILTER

(71) Applicant: Intel Corporation, Santa Clara, CA (US)

(72) Inventor: Matthew D. Pickett, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 265 days.

(21) Appl. No.: 16/064,047

(22) PCT Filed: Dec. 23, 2015

(86) PCT No.: PCT/US2015/000314
§ 371 (c)(1),
(2) Date: Jun. 20, 2018

(87) PCT Pub. No.: WO2017/111793
PCT Pub. Date: Jun. 29, 2017

(65) Prior Publication Data
US 2018/0368777 A1    Dec. 27, 2018

(51) Int. Cl.
*A61B 5/00* (2006.01)
*A61B 5/024* (2006.01)
(Continued)

(52) U.S. Cl.
CPC .......... *A61B 5/721* (2013.01); *A61B 5/00* (2013.01); *A61B 5/024* (2013.01);
(Continued)

(58) Field of Classification Search
None
See application file for complete search history.

(56) References Cited

U.S. PATENT DOCUMENTS

| | | | |
|---|---|---|---|
| 8,998,815 B2 | 4/2015 | Venkatraman et al. | |
| 2005/0075553 A1* | 4/2005 | Sakai | A61B 5/721 |
| | | | 600/372 |

(Continued)

FOREIGN PATENT DOCUMENTS

| | | |
|---|---|---|
| EP | 2229880 A1 | 9/2010 |
| WO | WO-2017111793 A1 | 6/2017 |

OTHER PUBLICATIONS

"International Application Serial No. PCT/US2015/000314, International Search Report dated Sep. 23, 2016", 4 pgs.

(Continued)

*Primary Examiner* — Ankit D Tejani
(74) *Attorney, Agent, or Firm* — Schwegman Lundberg & Woessner, P.A.

(57) ABSTRACT

Various systems and methods for implementing frequency domain adaptive motion cancellation filters. An example method includes receiving an optical signal representative of a physiological function. The example method further includes receiving a motion signal from an accelerometer. From the motion signal, a known motion spectrum is expressed as a sum of a product of coefficients for each component of the motion spectrum, wherein the coefficients are representative of the strength of the coupling between the motion signal and the optical signal. The example method may further include determining the coefficients of the motion spectrum using gradient descent and generating a decontaminated optical signal based on the optical signal and the motion model spectrum. Other systems, apparatuses, and methods are described.

21 Claims, 4 Drawing Sheets

(51) Int. Cl.
*A61B 5/11* (2006.01)
*G06F 17/16* (2006.01)

(52) U.S. Cl.
CPC ............ *A61B 5/02416* (2013.01); *A61B 5/11* (2013.01); *A61B 5/6824* (2013.01); *A61B 5/7225* (2013.01); *G06F 17/16* (2013.01); *A61B 5/681* (2013.01); *A61B 2562/0219* (2013.01)

(56) References Cited

U.S. PATENT DOCUMENTS

| | | |
|---|---|---|
| 2006/0094943 A1 | 5/2006 | Van Slyke |
| 2010/0113948 A1 | 5/2010 | Yang et al. |
| 2011/0054272 A1* | 3/2011 | Derchak ............ A61B 5/14542 600/301 |
| 2011/0066381 A1* | 3/2011 | Garudadri ............ A61B 5/0024 702/19 |
| 2011/0098583 A1 | 4/2011 | Pandia et al. |
| 2011/0257551 A1 | 10/2011 | Banet et al. |
| 2014/0018635 A1 | 1/2014 | Buchheim et al. |

OTHER PUBLICATIONS

"International Application Serial No. PCT/US2015/000314, Written Opinion dated Sep. 23, 2016", 5 pgs.

Cennini, Giovanni, et al., "Heart rate monitoring via remote photoplethysmography with motion artifacts reduction", Optics Express vol. 18, Issue 5, (Feb. 24, 2010), 4867-4875.

\* cited by examiner

FREQUENCY DOMAIN ADAPTIVE MOTION CANCELLATION FILTER

CROSS-REFERENCE TO RELATED APPLICATION

This application is a U.S. National Stage Filing under 35 U.S.C. 371 from International Application No. PCT/US2015/000314, filed on Dec. 23, 2015, and published as WO 2017/111793, which application is incorporated herein by reference in its entirety.

TECHNICAL FIELD

Embodiments described herein generally relate to sensors for physiological functions and in particular, to optical heart rate sensors.

BACKGROUND

Optical heart rate sensors may be coupled to the user's wrist in an unpredictable way such that the strength of that coupling varies significantly from person to person and from usage to usage. When the sensor is weakly coupled, even moderate motion may cause the sensor to bounce, resulting in motion coupling in which the amount of light reflected into the sensor responds strongly to motion. When motion is periodic and overlaps the frequency range of a heart rate, motion coupling may generate peaks in the power spectrum that cannot be distinguished from spectral peaks that come from the desired photoplethysmography (PPG) signal.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

In the following description, for purposes of explanation, numerous specific details are set forth in order to provide a thorough understanding of some example embodiments. It will be evident, however, to one skilled in the art that the present disclosure may be practiced without these specific details.

Figure 1:
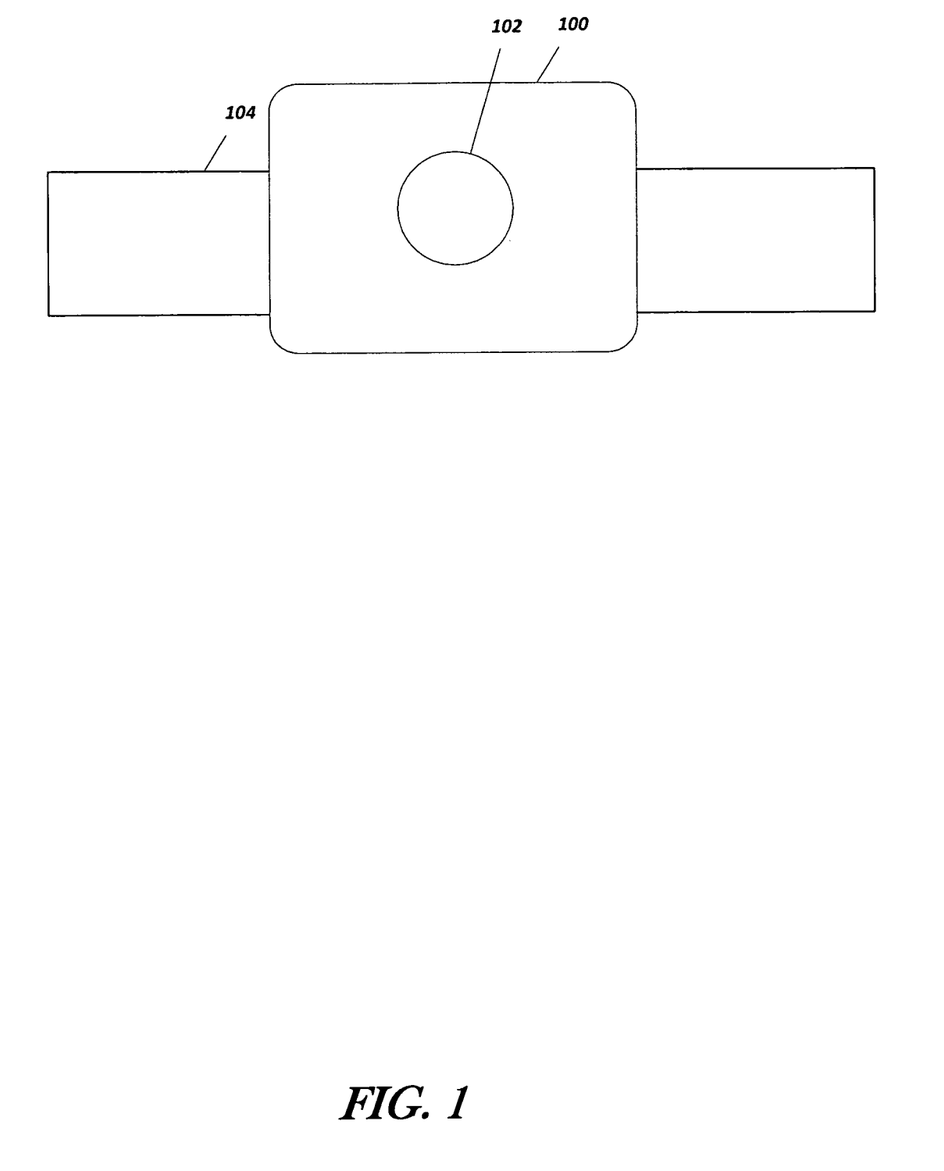
FIG. 1 is a bottom view of a wearable device, according to an embodiment.

FIG. 1 is a bottom view of a wearable device 100, according to an embodiment. The wearable device may include an optical heart rate monitor (OHRM). In an OHRM, light from a light emitting diode (LED) 102 is made incident on the human skin at, for example, a finger or a wrist. As the light enters the skin, the light is reflected from bodily components such as tissue, bones, veins, arteries, etc. Light reflected from the arterial blood has a time variant (AC). A photodiode receives the reflected light and converts it to a current. The profile of the signal is referred to as a photoplethysmography (PPG) signal.

OHRMs may be coupled to the user's wrist in an unpredictable way and the strength of that coupling varies significantly from person to person and even between times that the same person cinches the bands 104 on their OHRM. When the OHRM is weakly coupled, the OHRM may bounce around on the skin under even moderate motion, causing the amount of light reflected into the sensor to respond strongly to motion, a situation referred to as motion coupling. When motion is periodic and overlaps the frequency range of a heart rate, there may be a very strong peak in the power spectrum of the optical signal that comes exclusively from motion coupling. When this occurs, spectrum classifiers cannot distinguish between spectral peaks that come from a PPG signal and those that come from motion. Motion coupling is very common: almost all subjects exhibit moderate to severe motion coupling during periodic cardio exercises like walking, running, biking, and jumping jacks.

Systems, apparatuses, and methods in accordance with various embodiments address these and other concerns by using an adaptive filter to cancel out motion coupling from the optical heart rate signal. The cancellation process described herein iteratively solves an optimization problem for every spectrum, every second, and accordingly will be relatively uncomplicated and computationally inexpensive.

Figure 2:
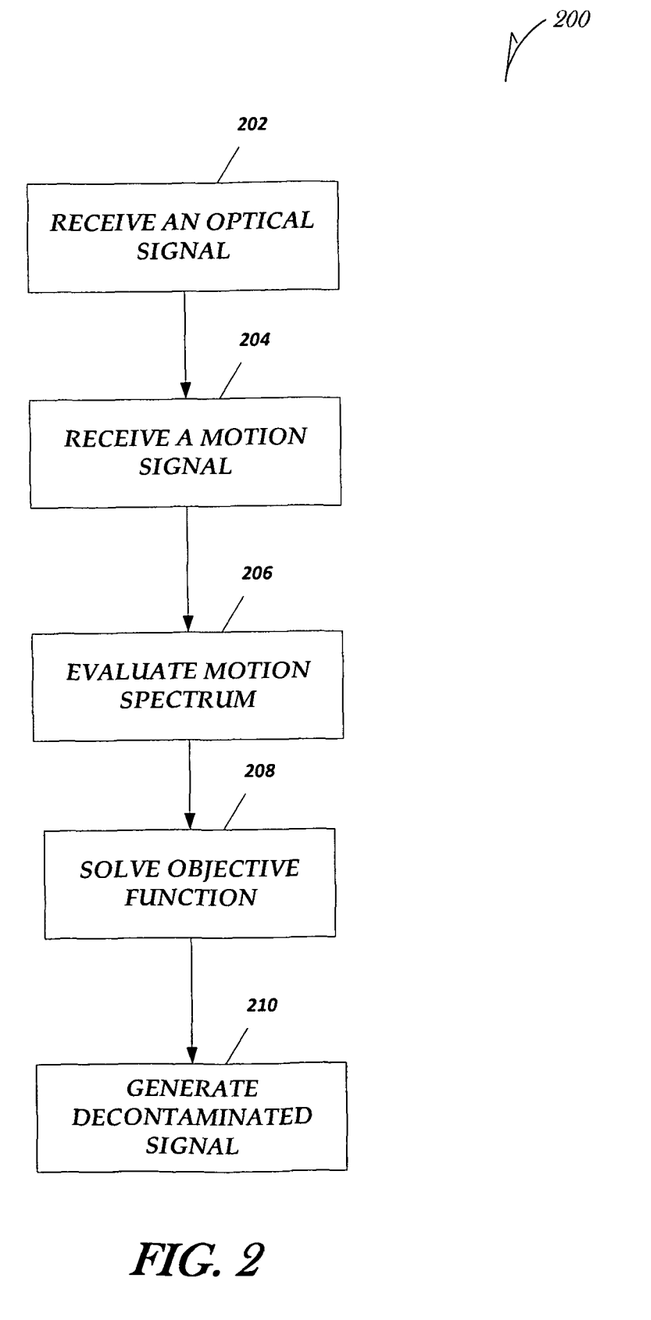
FIG. 2 is a flowchart illustrating a method of implementing frequency domain adaptive motion cancellation, according to an embodiment.

FIG. 2 is a flowchart illustrating a method 200 of implementing frequency domain adaptive motion cancellation, according to an embodiment.

The example method 200 begins with operation 202 with receiving an optical signal representative of a physiological function.

The example method 200 continues with operation 204 with receiving a motion signal from an accelerometer.

The example method 200 continues with operation 206 with evaluating a motion spectrum, based on the motion signal, expressed as a sum of a product of coefficients for axial components (e.g., components along an x-axis, y-axis, or z-axis, or any combination thereof, although embodiments are not limited thereto) of the motion spectrum to generate an expression of a motion model. Mathematically, the motion contamination $f_m$ present in an optical signal may be expressed as a linear combination of x, y, and z spectra $f_x$, $f_y$ and $f_z$:

$$f_m = c_x f_x + c_y f_y + c_z f_z \quad (1)$$

Contamination may be modeled as a linear process such that the residual or motion-compensated spectrum $f_r$ is the difference between the measured optical spectrum $f_o$ and the motion spectrum $f_m$:

$$f_r = f_o - f_m \quad (2)$$

The example method 200 continues with operation 208 with solving an objective function to determine values for the coefficients $c_x$, $c_y$, and $c_z$ wherein the coefficients $c_x$, $c_y$, and $c_z$ are representative of the strength of motion signal coupling to the optical signal, thereby generating the motion model. The optimization to solve for the coefficients $c_x$, $c_y$, and $c_z$ may be set up to minimize two terms: the L2 norm of the residuals, $\|f_r\|_2^2$, as well as the scaled L1 norm of the coefficient vector, $\lambda(c_x + c_y + c_z)$. This gives the optimization problem:

$$\min_{c_x, c_y, c_z} \|f_r\|_2^2 + \lambda(c_x + c_y + c_z) \quad (3)$$

The L2 term in the problem given by (3) serves the purpose of trying to find the coefficients $c_x$, $c_y$, and $c_z$ that eliminate as much as possible of the uncompensated optical spectrum. As a more specific example, if there is a large coincident peak in both $f_o$ and $f_x$ the L2 penalty will encourage $c_x$ to increase in order to reduce the magnitude of the residuals. As will be appreciated, given the L2 penalty term alone will tend to encourage coefficients $c_x$, $c_y$, and $c_z$ to become arbitrarily large, even when there is no spectral overlap. Accordingly, the L1 term is added to provide regularization by penalizing larger coefficient vectors. Accordingly, in the case of large coincident peaks, the regularization term L1 will tend to keep the coefficients $c_x$, $c_y$, and $c_z$ from becoming large, thereby preventing overzealous cancellation. The relative strength of L1 and L2 penalties is parameterized by $\lambda$ which is tuned during validation studies.

Embodiments apply various assumptions. For example, the motion model is assumed to be a linear combination of motion signals $f_x$, $f_y$, and $f_z$. Embodiments also assume that the motion spectrum $f_m$ may be linearly subtracted from the optical spectrum $f_o$. Due at least in part to these assumptions, solving the objective function may be performed or implemented using gradient descent, in which local minimums of a function are found by taking steps proportional to the negative of the gradient of the function at the current point.

The evaluation of the gradient of the objective function (wherein the objective function is given by Equation (3)) may be simplified to a 3×3 matrix multiplication at each iteration. This matrix multiplication is not computationally expensive and will not present performance bottlenecks. The calculation of the gradient is described below.

The objective function $\varepsilon$ and residual $f_r$ of the motion model may be described in matrix form to allow for solving its Jacobian using matrix calculus:

$$\varepsilon = \Sigma \cdot (f_r * f_r) + \Sigma \cdot (\lambda c) \quad (4)$$

$$f_r = f_o - [f_x f_y f_z] \cdot c \quad (5)$$

where $\Sigma$ is a summation matrix and $c$ is a coefficient vector of coefficients $c_x$, $c_y$, and $c_z$.

Next, the differential of the objective functions is evaluated with respect to the coefficient vector c:

$$d\varepsilon = \Sigma \cdot d(f_r * f_r) + \lambda \Sigma \cdot dc \quad (6)$$

The differential term of the residual $f_r$ is evaluated according to:

$$d(f_r * f_r) = 2\text{diag}(f_r) \cdot df_r \quad (7)$$

$$df_r = -[f_x f_y f_z] \cdot dc \quad (8)$$

Substituting terms back into (6) gives:

$$d\varepsilon = -\Sigma \cdot 2\text{diag}(f_r) \cdot [f_x f_y f_z] \cdot dc + \lambda \Sigma \cdot dc \quad (9)$$

This yields a Jacobian matrix of:

$$J = -\Sigma \cdot 2\text{diag}(f_r) \cdot [f_x f_y f_z] + \lambda \Sigma \quad (10)$$

The gradient g of a scalar function with respect to a vector is its adjoint Jacobian:

$$g = J^T = \begin{bmatrix} f_x \\ f_y \\ f_z \end{bmatrix} \cdot 2\text{diag}(f_r) \cdot 1 + \lambda 1 \quad (11)$$

Simplification of the gradient g yields:

$$g = -2 \begin{bmatrix} f_x \\ f_y \\ f_z \end{bmatrix} \cdot (f_o - [f_x f_y f_z] \cdot c) + \lambda 1 \quad \text{Or} \quad (12)$$

$$g = -2 \begin{bmatrix} f_x f_x & f_x f_y & f_x f_z \\ f_x f_y & f_y f_y & f_y f_z \\ f_x f_z & f_y f_z & f_z f_z \end{bmatrix} \cdot c - 2 \begin{bmatrix} f_x f_o \\ f_y f_o \\ f_z f_o \end{bmatrix} + \begin{bmatrix} \lambda \\ \lambda \\ \lambda \end{bmatrix} \quad (13)$$

The optimization problem may be solved by gradient descent with:

$$c_n = c_{n-1} - \Gamma g(c_{n-1}) \quad (14)$$

where $\Gamma$ is a rate parameter to be tuned by validation data and $c_n$ is a vector of coefficients $c_x$, $c_y$, and $c_z$.

$\Gamma$ should be set to a value that is not overly large, or Equation (14) will fail to converge on a set of coefficients $c_x$, $c_y$, and $c_z$. If $\Gamma$ is too small computational speed gains will not be achieved and bottlenecks and slowdowns will be observed.

After solution of coefficients $c_x$, $c_y$, and $c_z$, the example method 200 continues with operation 210 with generating the decontaminated signal. The residual or motion-compensated spectrum $f_r$ is calculated by subtracting the motion model spectrum from the optical spectrum (see Equation (2)). Embodiments then provide normalization and offset procedures to ensure that the average output value is zero. These procedures are performed so that the downstream classifier receives normalized data, a procedure often used in machine learning to make the classifier more robust and easier to train. The normalized residual spectrum may be stored as 8-bit integers and therefore algorithms will use a scaling constant that is determined through validation on real data. The normalized residual spectrum may be given by:

$$f_{r,n} = \frac{f_r - \text{mean}(f_r)}{\|f_r - \text{mean}(f_r)\|_2} \quad (15)$$

The decontaminated signal is provided for further processing to detect a parameter of the physiological function (e.g., a heart rate).

Embodiments described herein provide an adaptive filter that take as inputs an optical spectrum and accelerometer spectra and cancels a linear combination of the accelerometer spectra from the optical spectrum. Accordingly, motion bands caused by motion coupling are removed from the optical spectrum to provide a decontaminated PPG signal that may be analyzed according to optical monitoring methods to generate a reading such as a heart rate.

As described above with respect to Equations (3)-(14), embodiments use gradient descent in an iterative process to solve for coefficients $c_x$, $c_y$ and $c_z$ that minimize an objective function (Equation (3)) by iteratively stepping in a direction that is calculated to decrease the objective function (see Equation (14)).

Figure 3:
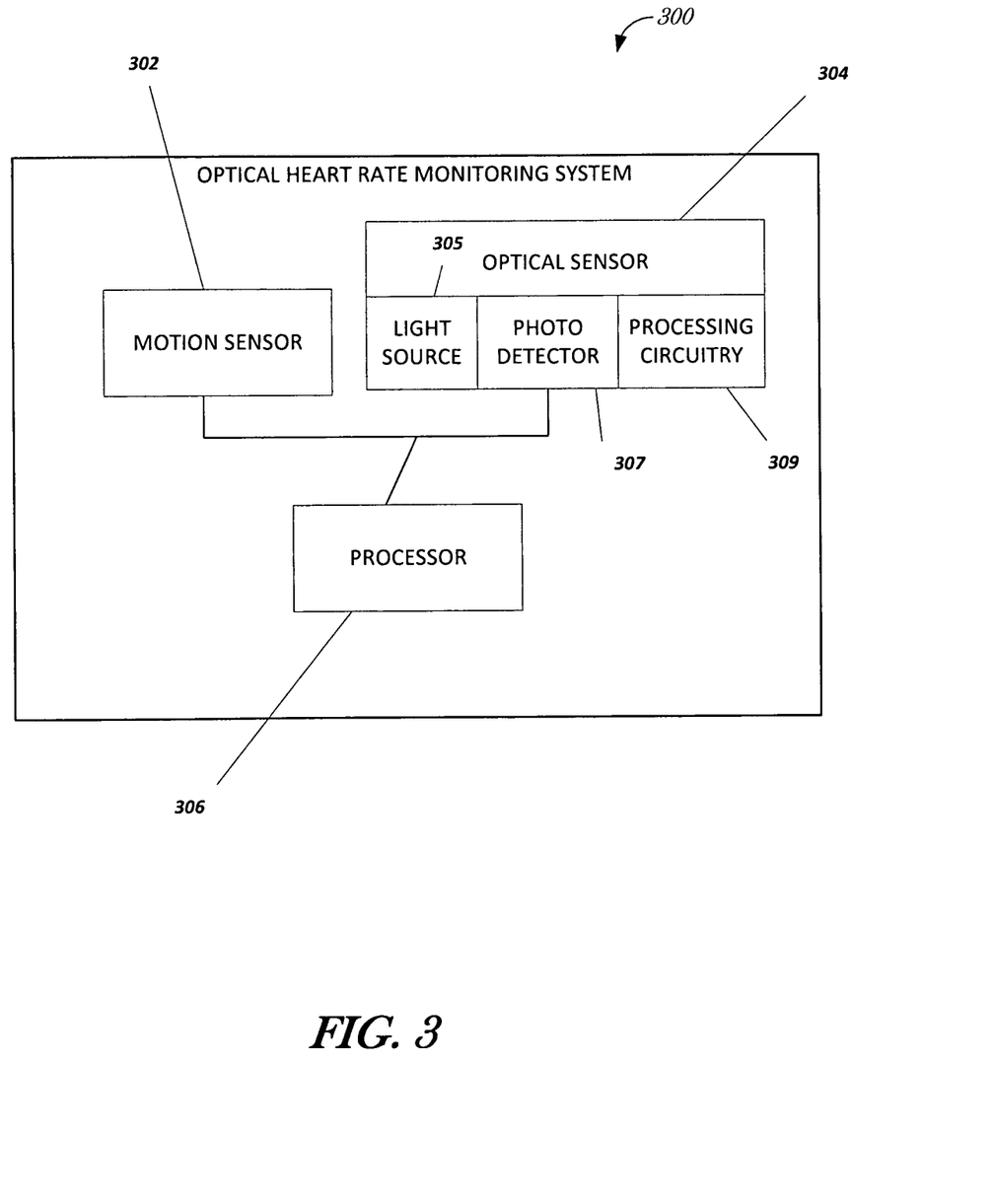
FIG. 3 is a block diagram illustrating an optical heart rate monitor (OHRM) system incorporated into a wearable device, according to an embodiment.

FIG. 3 is a block diagram illustrating an OHRM system 300 incorporated into a wearable device, according to an embodiment. The system 300 may include a motion sensor 302, an optical sensor 304, and one or more processors 306. The processor/s 306 may be coupled to receive signals from the motion sensor 302 and the optical sensor 304. For example, the processor/s 306 may be configured to receive an optical signal representative of a physiological function from the optical sensor 304. The processor/s 306 may further be configured to receive a motion signal from the motion sensor 302. In an embodiment, the wearable device comprises a smartwatch, although it is understood that any wearable device may be used. The motion sensor 302 may be configured to provide a motion signal representative of motion by a user wearing the apparatus. The motion sensor 302 may include an accelerometer or gyroscope.

The optical sensor 304 may include a periodic light source 305, a photo detector 307 positioned to receive periodic light emitted by the light source 305, and processing circuitry 309 to detect a parameter of physiological function of a user based on input from the photo detector 307.

The processor 306 may be configured to perform operations described earlier herein with respect to Equations (1)-(15). For example, the processor 306 may evaluate a motion spectrum, based on the motion signal, expressed as a sum of a product of coefficients for axial components of the motion spectrum to generate an expression of a motion model. The axial components may include at least two of an x-axis component of motion, a y-axis component of motion, and a z-axis component of motion.

The processor 306 may solve an objective function to determine values for the coefficients, wherein the coefficients are representative of the strength of motion signal coupling to the optical signal, to generate the motion model. Further, the processor 306 may generate a decontaminated signal based on the motion model and the optical signal. The processor 306 may provide the decontaminated signal for processing to detect a parameter of the physiological function. The processor 306 may solve the objective function by implementing gradient descent. In some examples, solving the objective function may include solving an equation according to $c_n = c_{n-1} - \Gamma g(c_{n-1})$, where $\Gamma$ is a rate parameter to be tuned by validation data, $c_n$ is a vector of coefficients for axial components of the motion spectrum, and g represents the gradient of the motion spectrum at a point. Each operation may be performed in the frequency domain.

Embodiments may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

A processor subsystem may be used to execute the instruction on the machine-readable medium. The processor subsystem may include one or more processors, each with one or more cores. Additionally, the processor subsystem may be disposed on one or more physical devices. The processor subsystem may include one or more specialized processors, such as a graphics processing unit (GPU), a digital signal processor (DSP), a field programmable gate array (FPGA), or a fixed function processor.

Examples, as described herein, may include, or may operate on, logic or a number of components, modules, or mechanisms. Modules may be hardware, software, or firmware communicatively coupled to one or more processors in order to carry out the operations described herein. Modules may be hardware modules, and as such modules may be considered tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

Figure 4:
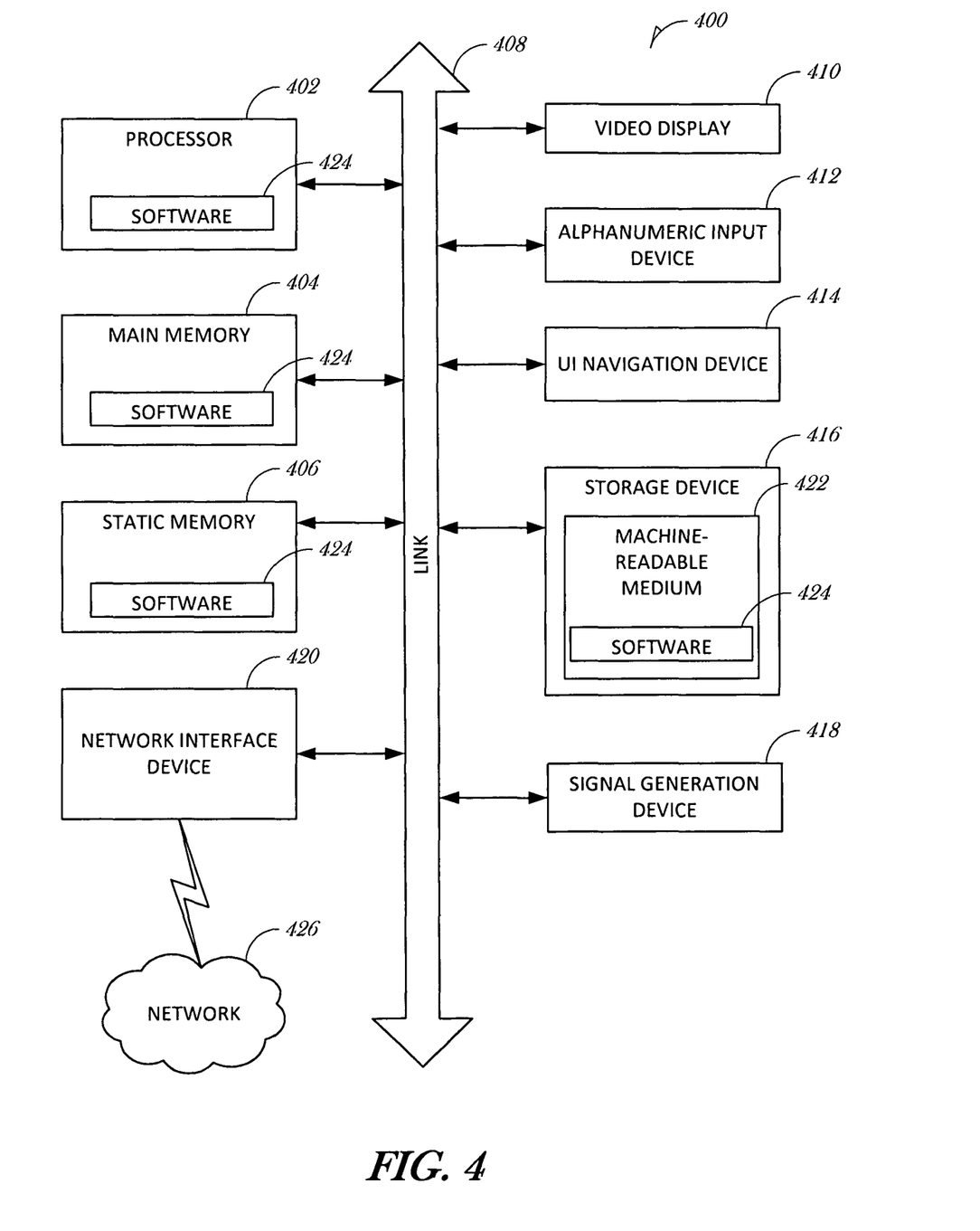
FIG. 4 is a block diagram illustrating an example machine upon which any one or more of the techniques (e.g., methodologies) discussed herein may perform, according to an example embodiment.

FIG. 4 is a block diagram illustrating a machine in the example form of a computer system 400, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be an onboard vehicle system, wearable device, personal computer (PC), a tablet PC, a hybrid tablet, a personal digital assistant (PDA), a mobile telephone, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 400 includes at least one processor 402 (e.g., a central processing unit (CPU), a graphics processing unit (GPU) or both, processor cores, compute nodes, etc.), a main memory 404 and a static memory 406, which communicate with each other via a link 408 (e.g., bus). The computer system 400 may further include a video display unit 410, an alphanumeric input device 412 (e.g., a keyboard), and a user interface (UI) navigation device 414 (e.g., a mouse). In one embodiment, the video display unit 410, input device 412 and UI navigation device 414 are incorporated into a touch screen display. The computer system 400 may additionally include a storage device 416 (e.g., a drive unit), a signal generation device 418 (e.g., a speaker), a network interface device 420, and one or more sensors (not shown), such as a global positioning system (GPS) sensor, compass, accelerometer, gyrometer, magnetometer, or other sensor.

The storage device 416 includes a machine-readable medium 422 on which is stored one or more sets of data structures and instructions 424 (e.g., software) embodying or utilized by any one or more of the methodologies or functions described herein. The instructions 424 may also reside, completely or at least partially, within the main memory 404, static memory 406, and/or within the processor 402 during execution thereof by the computer system 400, with the main memory 404, static memory 406, and the processor 402 also constituting machine-readable media.

While the machine-readable medium 422 is illustrated in an example embodiment to be a single medium, the term "machine-readable medium" may include a single medium or multiple media (e.g., a centralized or distributed database, and/or associated caches and servers) that store the one or more instructions 424. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 424 may further be transmitted or received over a communications network 426 using a transmission medium via the network interface device 420 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Bluetooth, Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Additional Notes & Examples

The following non-limiting list of examples may further illustrate the present systems and method suitable for use in demodulating a signal from an intermittently illuminated region.

In Example 1, a method may include receiving an optical signal representative of a physiological function; receiving a motion signal from an accelerometer; receiving a motion signal from an accelerometer; evaluating a motion spectrum, based on the motion signal, expressed as a sum of a product of coefficients for axial components of the motion spectrum to generate an expression of a motion model; solving an objective function to determine values for the coefficients, wherein the coefficients are representative of the strength of motion signal coupling to the optical signal, to generate the motion model; and generating a decontaminated signal based on the motion model and the optical signal.

In Example 2, the subject matter of Example 1 may optionally include providing the decontaminated signal for processing to detect a parameter of the physiological function.

In Example 3, the subject matter of any of Examples 1-2 may optionally include wherein solving the objective function includes implementing gradient descent.

In Example 4, the subject matter of any of Examples 1-3 may optionally include wherein solving the objective function includes solving an equation according to $c_n = c_{n-1} - \Gamma g(c_{n-1})$, where $\Gamma$ is a rate parameter to be tuned by validation data, $c_n$ is a vector of coefficients for axial components of the motion spectrum, and g represents the gradient of the motion spectrum at a point.

In Example 5, the subject matter of any of Examples 1-4 may optionally include wherein each operation is performed in the frequency domain.

In Example 6, the subject matter of any of Examples 1-5 may optionally include wherein the axial components include at least two of an x-axis component of motion, a y-axis component of motion, and a z-axis component of motion.

In Example 7, the subject matter of any of Examples 1-6 may optionally include wherein the decontaminated signal is calculated as a difference between a measured optical spectrum $f_o$ and a motion spectrum $f_m$, and wherein the method further includes a normalization operation.

Example 8 is an apparatus (e.g., for a heart rate monitor or other monitor of a physiological function) comprising: an accelerometer configured to provide a motion signal representative of motion by a user wearing the apparatus; an optical sensor; and one or more processors to receive an optical signal representative of a physiological function from the optical sensor; receive a motion signal from the accelerometer; evaluate a motion spectrum, based on the motion signal, expressed as a sum of a product of coefficients for axial components of the motion spectrum to generate an expression of a motion model; solve an objective function to determine values for the coefficients, wherein the coefficients are representative of the strength of motion signal coupling to the optical signal, to generate the motion model; and generate a decontaminated signal based on the motion model and the optical signal.

In Example 9, the subject matter of Example 8 may optionally include wherein the one or more processors are further configured to provide the decontaminated signal for processing to detect a parameter of the physiological function.

In Example 10, the subject matter of any of Examples 8-9 may optionally include wherein solving the objective function includes implementing gradient descent.

In Example 11, the subject matter of any of Examples 8-10 may optionally include wherein solving the objective function includes solving an equation according to $c_n = c_{n-1} - \Gamma g(c_{n-1})$, where $\Gamma$ is a rate parameter to be tuned by validation data, $c_n$ is a vector of coefficients for axial components of the motion spectrum, and g represents the gradient of the motion spectrum at a point.

In Example 12, the subject matter of any of Examples 8-11 may optionally include wherein each operation is performed in the frequency domain.

In Example 13, the subject matter of any of Examples 8-12 may optionally include wherein the axial components include at least two of an x-axis component of motion, a y-axis component of motion, and a z-axis component of motion.

In Example 14, the subject matter of any of Examples 8-13 may optionally include wherein the decontaminated signal is calculated as a difference between a measured optical spectrum $f_o$ and a motion spectrum $f_m$, and wherein the method further includes a normalization operation.

Example 15 is a computer-readable storage medium that stores instructions for execution by one or more processors to perform operations for optical monitoring of physiological functions, the operations to configure the one or more processors to receive an optical signal representative of a physiological function; receive a motion signal from an accelerometer; evaluate a motion spectrum, based on the motion signal, expressed as a sum of a product of coefficients for axial components of the motion spectrum to generate an expression of a motion model; solve an objective function to determine values for the coefficients, wherein the coefficients are representative of the strength of motion signal coupling to the optical signal, to generate the motion model; and generate a decontaminated signal based on the motion model and the optical signal.

In Example 16, the subject matter of Example 15 may optionally include wherein the operations further configure the one or more processors to provide the decontaminated signal for processing to detect a parameter of the physiological function.

In Example 17, the subject matter of any of Examples 15-16 may optionally include wherein solving the objective function includes implementing gradient descent.

In Example 18, the subject matter of any of Examples 15-17 may optionally include wherein the operations further configure the one or more processors to solve an equation according to $c_n = c_{n-1} - \Gamma g(c_{n-1})$, where $\Gamma$ is a rate parameter to be tuned by validation data, $c_n$ is a vector of coefficients for axial components of the motion spectrum, and g represents the gradient of the motion spectrum at a point.

In Example 19, the subject matter of any of Examples 15-18 may optionally include wherein each operation is performed in the frequency domain.

In Example 20, the subject matter of any of Examples 15-19 may optionally include wherein the axial components include at least two of an x-axis component of motion, a y-axis component of motion, and a z-axis component of motion.

In Example 21, the subject matter of any of Examples 15-20 may optionally include wherein the decontaminated signal is calculated as a difference between a measured optical spectrum $f_o$ and a motion spectrum $f_m$, and wherein the method further includes a normalization operation.

Example 22 is a system comprising means for receiving an optical signal representative of a physiological function; means for receiving a motion signal from an accelerometer; means for evaluating a motion spectrum, based on the motion signal, expressed as a sum of a product of coefficients for axial components of the motion spectrum to generate an expression of a motion model; means for solving an objective function to determine values for the coefficients, wherein the coefficients are representative of the strength of motion signal coupling to the optical signal, to generate the motion model; and means for generating a decontaminated signal based on the motion model and the optical signal.

In Example 23, the subject matter of Example 22 may optionally include means for providing the decontaminated signal for processing to detect a parameter of the physiological function.

In Example 24, the subject matter of any of Examples 22-23 may optionally include means for implementing gradient descent.

In Example 25, the subject matter of any of Examples 22-24 may optionally include means for solving an equation according to $c_n = c_{n-1} - \Gamma g(c_{n-1})$, here $\Gamma$ is a rate parameter to be tuned by validation data, $c_n$ is a vector of coefficients for axial components of the motion spectrum, and g represents the gradient of the motion spectrum at a point.

Example 26 is a computer-readable storage medium that stores instructions for execution by one or more processors to perform operations for optical monitoring of physiological functions, the operations to configure the one or more processors to implement any one of the methods described herein.

Example 27 is a system comprising means to implement any of the methods described herein.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. In addition, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. An apparatus comprising:
    an accelerometer configured to provide a motion signal representative of motion by a user wearing the apparatus;
    an optical sensor; and
    one or more processors to
        receive an optical signal representative of a physiological function from the optical sensor;
        receive a motion signal from the accelerometer;
        evaluate a motion spectrum, based on the motion signal, expressed as a sum of a product of coefficients for axial components of the motion spectrum to generate an expression of a motion model;
        solve an objective function to determine values for the coefficients, wherein the coefficients are representative of the strength of motion signal coupling to the optical signal, to generate the motion model; and
        generate a decontaminated signal based on the motion model and the optical signal.

2. The apparatus of claim 1, wherein the one or more processors are further configured to:
    provide the decontaminated signal for processing to detect a parameter of the physiological function.

3. The apparatus of claim 1, wherein solving the objective function includes implementing gradient descent.

4. The apparatus of claim 3, wherein solving the objective function includes solving an equation according to $c_n = c_{n-1} - \Gamma g(c_{n-1})$,
    where $\Gamma$ is a rate parameter to be tuned by validation data, $c_n$ is a vector of coefficients for axial components of the motion spectrum, and g represents the gradient of the motion spectrum at a point.

5. The apparatus of claim 1, wherein each operation is performed in the frequency domain.

6. The apparatus of claim 1, wherein the axial components include at least two of an x-axis component of motion, a y-axis component of motion, and a z-axis component of motion.

7. The apparatus of claim 1, wherein the decontaminated signal is calculated as a difference between a measured optical spectrum $f_o$ and a motion spectrum $f_m$, and wherein the method further includes a normalization operation.

8. A method comprising:
    receiving an optical signal representative of a physiological function;
    receiving a motion signal from an accelerometer;
    evaluating a motion spectrum, based on the motion signal, expressed as a sum of a product of coefficients for axial components of the motion spectrum to generate an expression of a motion model;
    solving an objective function to determine values for the coefficients, wherein the coefficients are representative of the strength of motion signal coupling to the optical signal, to generate the motion model; and
    generating a decontaminated signal based on the motion model and the optical signal.

9. The method of claim 8, further comprising:
    providing the decontaminated signal for processing to detect a parameter of the physiological function.

10. The method of claim 8, wherein solving the objective function includes implementing gradient descent.

11. The method of claim 10, wherein solving the objective function includes solving an equation according to $c_n = c_{n-1} - \Gamma g(c_{n-1})$,
    where $\Gamma$ is a rate parameter to be tuned by validation data, $c_n$ is a vector of coefficients for axial components of the motion spectrum, and g represents the gradient of the motion spectrum at a point.

12. The method of claim 8, wherein each operation is performed in the frequency domain.

13. The method of claim 8, wherein the axial components include at least two of an x-axis component of motion, a y-axis component of motion, and a z-axis component of motion.

14. The method of claim 8, wherein the decontaminated signal is calculated as a difference between a measured optical spectrum $f_o$ and a motion spectrum $f_m$, and wherein the method further includes a normalization operation.

15. A non-transitory computer-readable storage medium that stores instructions for execution by one or more processors to perform operations for optical monitoring of physiological functions, the operations to configure the one or more processors to:
    receive an optical signal representative of a physiological function;
    receive a motion signal from an accelerometer;
    evaluate a motion spectrum, based on the motion signal, expressed as a sum of a product of coefficients for axial components of the motion spectrum to generate an expression of a motion model;
    solve an objective function to determine values for the coefficients, wherein the coefficients are representative of the strength of motion signal coupling to the optical signal, to generate the motion model; and
    generate a decontaminated signal based on the motion model and the optical signal.

16. The non-transitory computer-readable storage medium of claim 15, wherein the operations further configure the one or more processors to: provide the decontaminated signal for processing to detect a parameter of the physiological function.

17. The non-transitory computer-readable storage medium of claim 15, wherein solving the objective function includes implementing gradient descent.

18. The non-transitory computer-readable storage medium of claim 17, wherein the operations further configure the one or more processors to: solve an equation according to $c_n = c_{n-1} - \Gamma g(c_{n-1})$, where $\Gamma$ is a rate parameter to be tuned by validation data, $c_n$ is a vector of coefficients for axial components of the motion spectrum, and g represents the gradient of the motion spectrum at a point.

19. The non-transitory computer-readable storage medium of claim 15, wherein each operation is performed in the frequency domain.

20. The non-transitory computer-readable storage medium of claim 15, wherein the axial components include at least two of an x-axis component of motion, a y-axis component of motion, and a z-axis component of motion.

21. The non-transitory computer-readable storage medium of claim 15, wherein the decontaminated signal is calculated as a difference between a measured optical spectrum $f_o$ and a motion spectrum $f_m$, and wherein the method further includes a normalization operation.

* * * * *